United States Patent [19]
Taheri

[11] Patent Number: 5,849,030
[45] Date of Patent: Dec. 15, 1998

[54] SPLANCHNIC BLOOD SUPPLY WARMING DEVICE

[76] Inventor: Syde A. Taheri, 268 Dan-Troy, Williamsville, N.Y. 14221

[21] Appl. No.: 937,828

[22] Filed: Sep. 25, 1997

[51] Int. Cl.[6] .......................................................... A61F 7/00
[52] U.S. Cl. ............................................ 607/104; 607/105
[58] Field of Search ........................... 607/104, 108–112, 607/114; 126/204; 165/46

[56] References Cited

U.S. PATENT DOCUMENTS

| | | |
|---|---|---|
| 3,496,942 | 2/1970 | Shipley . |
| 4,111,209 | 9/1978 | Wolvek . |
| 4,154,245 | 5/1979 | Daily . |
| 4,522,640 | 6/1985 | Jagoe, III . |
| 4,844,074 | 7/1989 | Kurucz . |
| 5,072,875 | 12/1991 | Zacoi . |
| 5,190,032 | 3/1993 | Zacoi . |
| 5,456,702 | 10/1995 | Falk . |
| 5,531,776 | 7/1996 | Ward et al. . |
| 5,545,196 | 8/1996 | Falk . |
| 5,609,620 | 3/1997 | Daily . |
| 5,634,940 | 6/1997 | Panyard . |

*Primary Examiner*—Jennifer Bahr
*Assistant Examiner*—Roy D. Gibson
*Attorney, Agent, or Firm*—Hodgson, Russ, Andrews, Woods & Goodyear

[57] ABSTRACT

A bag apparatus for warming the splanchnic blood supply of a patient both during and after surgery to prevent the onset of hypothermia. A bag apparatus for selectively warming an internal organ. A method to prevent hypothermia in a patient during and after surgical procedures. A heating pad apparatus for warming the splanchnic blood supply in a patient during and after surgery, and methodology for accomplishing same.

17 Claims, 7 Drawing Sheets

SPLANCHNIC BLOOD SUPPLY WARMING DEVICE

BACKGROUND OF THE INVENTION

1. Field of the Invention

The present invention relates generally to an apparatus and method for warming a patient during and after surgery such that the patient's core temperature and splanchnic blood supply maintain a normothermic temperature.

There are documented over a million major surgical cases where patients have become hypothermic following surgery. Hypothermia is the cooling of the body below normal temperatures. Hypothermia greatly increases the risk of death during surgery in elderly people and others weakened due to disease or serious injury. Once a patient becomes hypothermic, quick action must be taken to reverse the cooling process. This action requires expenditure of time and resources to bring the patient's body temperature back to normal.

Present methods of warming a patient include blowing warm air onto the exposed surgery site, applying heated wraps to the body, and using external heating shields which are contoured to the shape of body part to be warmed.

There is presently no method to effectively provide heat to the splanchnic blood supply to ensure normothermic core temperatures both during and after surgery, so as to prevent hypothermia.

2. Prior Art

The prior art in this field is devoid of any effective method to supply heat to the splanchnic blood supply, which is the major blood supply in the body.

There are presently available several different types of external heating devices, ranging from simple heated wraps to more sophisticated external heating shields, which contour to the shape of the body part desired to be warmed. This is shown in U.S. Pat. No. 5,634,940 to Panyard. However, these types of devices nowhere teach or show how to prevent hypothermia in the patient, and nowhere show or teach how to provide a constant source of heat to the splanchnic blood supply.

Also, there are devices presently available which are designed to produce hypothermia in selected areas of the patient's body during surgery. These devices attempt to prevent damage to the organ by decreasing the organ's temperature to reduce metabolism, and this technique is shown in U.S. Pat. No. 5,609,620 to Daily, which illustrates a cardiac cooling jacket.

In U.S. Pat. No. 3,496,942 to Shipley is shown a heater for internal use. This patent shows a rigid nozzle adapted to be inserted into a body cavity, with an inflatable expandable bag wrapped around the nozzle. The nozzle has fluid holes in it, and the bag is filled with a warm solution supplied through the nozzle. The patent, however, nowhere teaches or shows the heating of the splanchnic blood supply, and nowhere shows or teaches how to prevent hypothermia in a patient during and after surgery. Further, its application is strictly limited to heating body cavities.

Finally, U.S. Pat. No. 5,531,776 to Ward shows a non-invasive core temperature manipulation apparatus. This patent requires a device to be extended into the patient's esophagus and has a heating or cooling element attached to the device which impinges the thoracic descending aorta, and heats or cools the descending thoracic aorta. However, there are numerous problems and limitations with this device. The device requires the patient's esophagus be cluttered with a bulky item for the entire duration of heating. This limits the types of surgical procedures in which the device can be used. Also, the device impinges upon the descending thoracic aorta, and partially occludes this aorta, resulting in an increased arterial pressure. Certainly, this result is not desirable in all patients, and could even be harmful or fatal to some patients due to perforation of the esophagus. Nowhere does this patent show or teach how to keep the splanchnic blood supply normothermic.

Hence, there is presently a great need for a device which can prevent or counter the effects of hypothermia by maintaining normothermic temperatures of the splanchnic blood supply. There is also a need for a device which can be used both during surgery, and after surgery to maintain the normothermic temperature of the splanchnic blood supply. There is also a need for a warming device which accomplishes this, yet avoids the problems and limitations of the prior art. The present invention provides both a device and method to accomplish this.

SUMMARY OF THE INVENTION

It is an objective of this invention to provide an apparatus for providing heat to the patient's abdominal organs and splanchnic blood supply during the timeframe when the surgery is being performed to prevent the onset of hypothermia, and during the timeframe following the surgery to prevent hypothermia.

It is a further objective of this invention to provide heat directly to the patient's visceral organs or skin while surgery is being performed on the patient.

It is a further objective of this invention to provide an apparatus capable of maintaining normothermic core temperatures of the patient's body both during and after surgery.

It is a further object of this invention to prevent heat loss from an open abdominal cavity in a patient during surgery.

It is a further object of this invention to provide a device which can supply heat to warm a specific selected internal organ such as the heart, lungs, kidneys, spleen, bowel, liver, and the like.

It is a further object of this invention to provide a device which can remain in the patient's body after surgery for an extended time, and for as long as required to achieve the desired heating.

It is a further object of this invention to provide an apparatus capable of heating the patient following surgery, yet removable from the patient's body without the need to reopen the patient's abdominal cavity.

Another object of this invention is to provide a methodology for preventing hypothermia in a patient undergoing, or just having undergone surgery. It is also an object of this invention to provide a methodology to keep a normothermic temperature of the splanchnic blood supply of a person undergoing or just having undergone surgery.

It is also an objective of this invention to provide a device which can supply heat directly to the bowel, remain against the bowel for as long as desired, yet be easily removable from the bowel.

The invention comprises a thin walled plastic bag, which can be rectangular, semicircular, or cylindrical in shape. The bag can also be constructed to conform to the shape of internal organs, such as the heart, spleen, liver, lungs, stomach, and the like. The bag contains a warm solution, preferably a saline solution or chemical solutions which generate heat.

The bag is placed against the bowel and the bag heats the splanchnic blood supply. There are two very thin walled pliable hollow tubes, one an inlet tube for supplying solution to the bag, and one an outlet tube for removing solution from the bag. These tubes both penetrate the bag, and serve to supply and remove solution from the bag. The inlet tube carries warm solution into the plastic bag from a solution reservoir. The outlet tube removes solution from the bag and returns the solution to the reservoir. Of course, impermeable seals exist where the inlet and outlet tubes penetrate the bag, such that the solution does not escape into the patient's body. A thin walled cotton sheath is placed over and covers the bag. Also, an irrigator tube is provided on the bag, so that the cotton sheath covering the bag remains moist.

The bag is placed in the patient's exposed abdominal cavity and allowed to contact the visceral organs of the patient Heat is radiated from the solution through the plastic bag walls, through the damp cotton sheath and into the patient's visceral organs. The purpose of keeping the cotton sheath damp is not only to increase heat conductivity, but the bag must be kept moist to prevent it from sticking to the patient's internal organs. Also, the bag can be placed directly against the bowel to keep the bowel warm and to transfer heat to the splanchnic blood supply as well as the aortic blood supply.

The heat from the warm solution in the bag is conducted through the bag and through the cotton sheath to the splanchnic blood supply, and warms this blood supply, resulting in a normothermic core temperature. Of course, as the patient's heart pumps, the warmed blood circulates to all the distal members of the body and warming them thoroughly as well.

As time progresses, the solution in the bag is maintained at a constant warm temperature. This is accomplished by constantly circulating warm solution from the reservoir into the inlet tube, and this constant source of warm solution displaces the solution in the bag, and this displaced solution exits the bag via the outlet tube. The solution then returns to the reservoir where it is rewarmed by a heating element in the reservoir. A pump is used to constantly move the solution from the reservoir, through a suction tube, through the pump, through a feeder tube, through the inlet tube, through the bag, out the outlet tube, and through a return tube which carries the solution back to the reservoir.

The reservoir is large enough such that the solution entering it from the return tube has no substantial effect on the constant temperature of the solution in the reservoir.

A thermometer may be used to monitor both the temperature of the solution reservoir, as well as the temperature of the patient's body. If necessary, the heating element can be adjusted to provide for a warmer or cooler solution, as each particular case may dictate. Also, the pump can be of a variable speed, such that the flow of the fluid through the tubes and bag can be adjusted. In extreme cases, when the patient's temperature is very low, the large difference in temperature between the warm solution in the bag and the body will cause the solution in the bag to cool more quickly. This may require that the pump speed be increased to accommodate such a situation. This might also require that the heating element supply additional heat to the reservoir, to maintain the reservoir temperature.

The present invention also allows the patient's splanchnic blood supply to continue receiving heat from the bag after the surgery is completed. When the patient is operated on, the bag is placed in the exposed abdominal cavity, against the bowel or other visceral organ, providing heat to the patient during surgery. If it is desired or necessary to continue supplying heat to the patient following surgery, this can be accomplished by the following procedure. Before closing the patient's abdomen or chest cavity, as the case may be, the surgeon creates a bag hole in the patient's side flank or chest, and inserts a bag hole tube in the bag hole. Next, the inlet and outlet tubes and an irrigator tube are placed through the bag hole tube, and the bag is placed against the internal organ. No cotton sheath is placed about the bag in this procedure. Next, the patient's abdominal cavity is sutured. The bag and tubes remain in the patient, and continue to supply heat to the splanchnic blood supply, or internal organs, until the threat of hypothermia has passed, or the desired heating has otherwise been achieved.

To facilitate removal of the bag, an irrigator tube supplies water to the surface of the bag, thereby wetting the bag so it will not stick to the internal organs. After removal, the bag is drained, and the bag, inlet, outlet, and irrigator tubes are all pulled through the bag hole. The bag hole tube is removed from the patient's side flank, and the bag hole is sutured by procedures well known to those of ordinary skill in the art. Then, the tubes and bag are discarded. Hence, reopening the abdominal cavity to remove the bag is avoided by the present invention.

In an alternative embodiment of the present invention, an exothermic heating pad replaces the bag and tubes previously discussed. The exothermic heating pad can be held directly against the bowel to heat the splanchnic blood supply. Likewise, the exothermic heating pad can be left in the patient, and removed through a pad hole and pad tube in the patient's side flank. In this embodiment, the heating pad has a removal cord to assist in pulling the bag through the pad tube in the patient's side flank. There is also an irrigator tube present to wet the surface of the pad prior to removing the pad through the pad hole. The pad, irrigator tube, and removal cord are all pulled through the pad hole after the heating is complete, and the pad tube is removed from the patient, and the pad hole is sutured by procedures well known to those of ordinary skill in the art.

BRIEF DESCRIPTION OF THE DRAWINGS

Briefly, the accompanying drawings of this invention show the following.

DETAILED DESCRIPTION OF THE PREFERRED EMBODIMENTS

Figure 2:
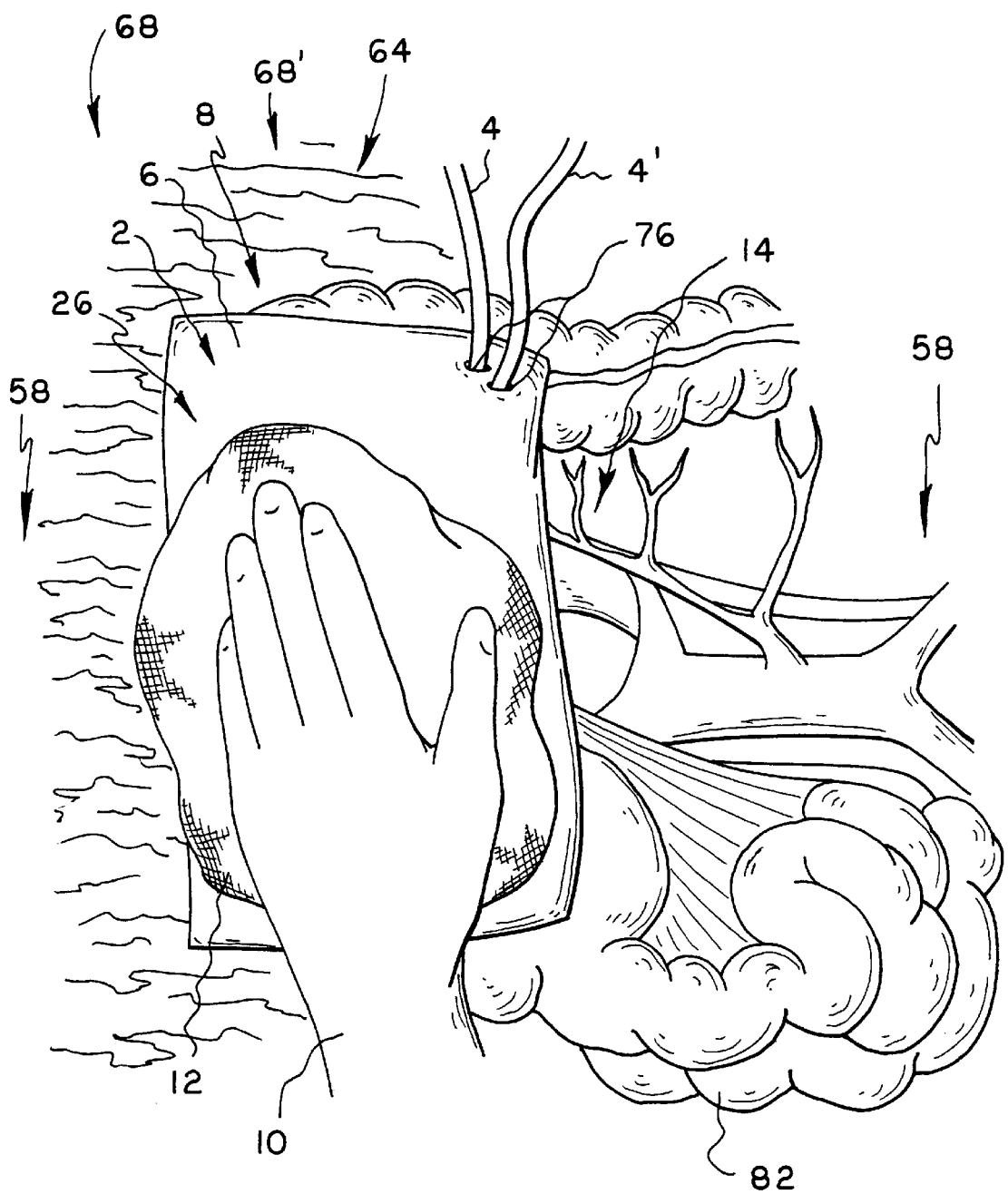
FIG. 2 is a plan view showing the present invention.
Figure 6:
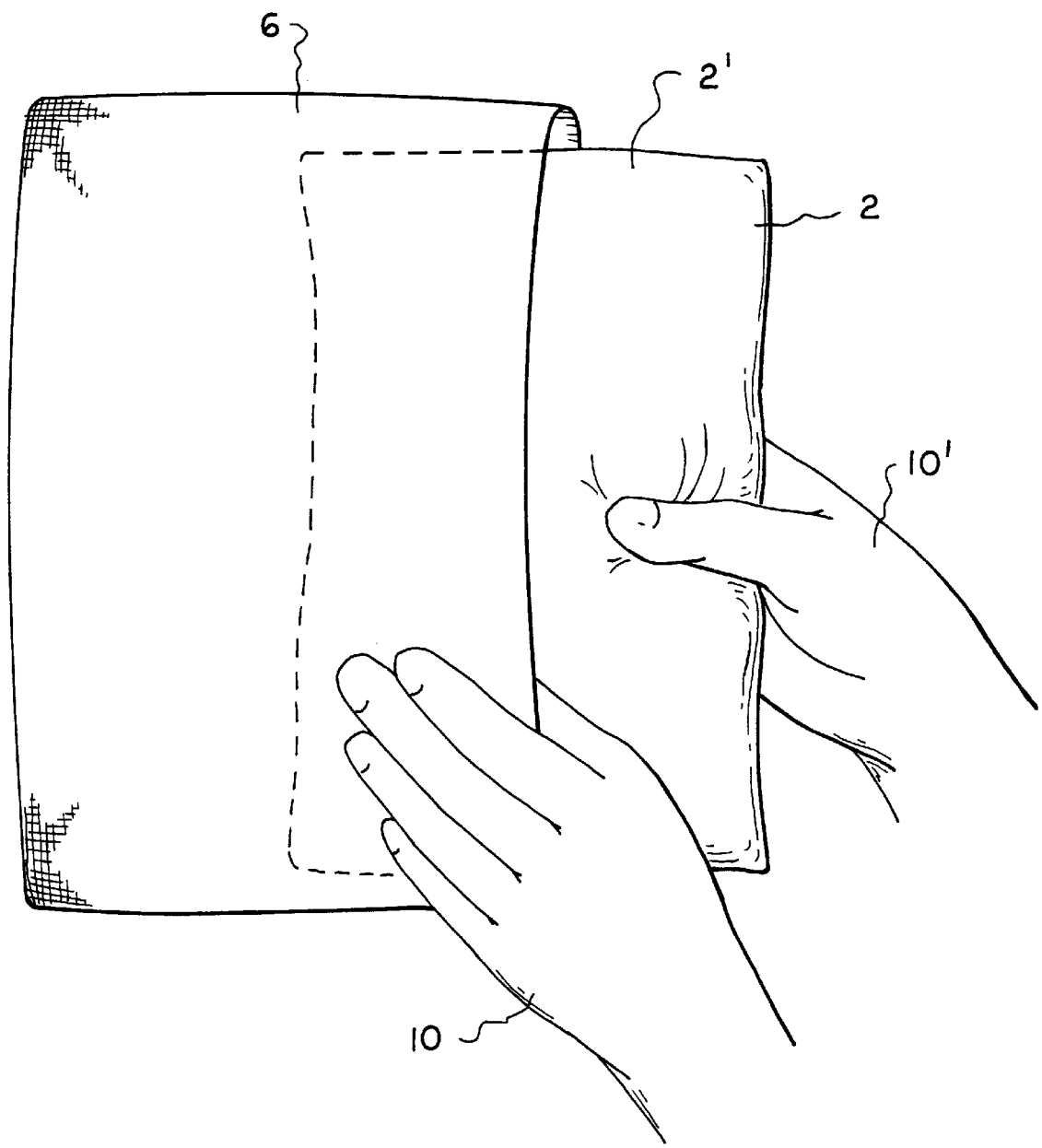
FIG. 6 is a plan view of the bag and cotton sheath.
Figure 7:
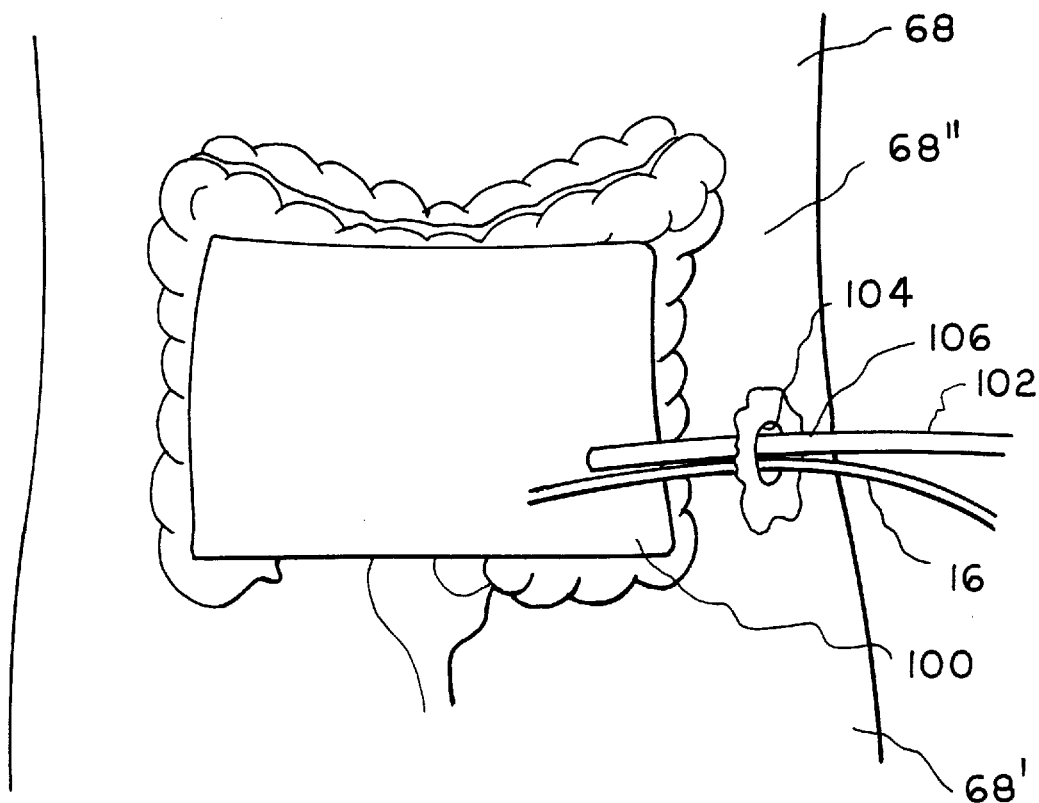
FIG. 7 is a plan view of the heating pad embodiment of the present invention.

Turning now to FIG. 2, the splanchnic blood supply warming device 8 is generally shown placed in the open abdominal cavity 64 of patient 68. The first step in preparing the splanchnic blood supply warming device 8 for use is best illustrated in FIG. 6, which shows hands 10 and 10$^1$ manually fitting bag means 2 into cotton sheath means 6. After this preparatory step, the splanchnic blood warming device is ready to use.

FIG. 2 shows the splanchnic blood supply warming device 8, as it would appear in actual operation. Reference number 10 shows a hand, and immediately underneath the hand is sterile buffer means 12. Under the sterile buffer 12 is the cotton sheath 6 and bag 2. The bag 2 contains a warm solution 26. Buffer 12 can be any sterile type gauze well known to those of ordinary skill in the art, but can also be of a material which has highly insulative properties. The use of an insulative buffer 12 prevents any heat from solution 26 in bag 2 from being conducted to hand 10.

Figure 5:
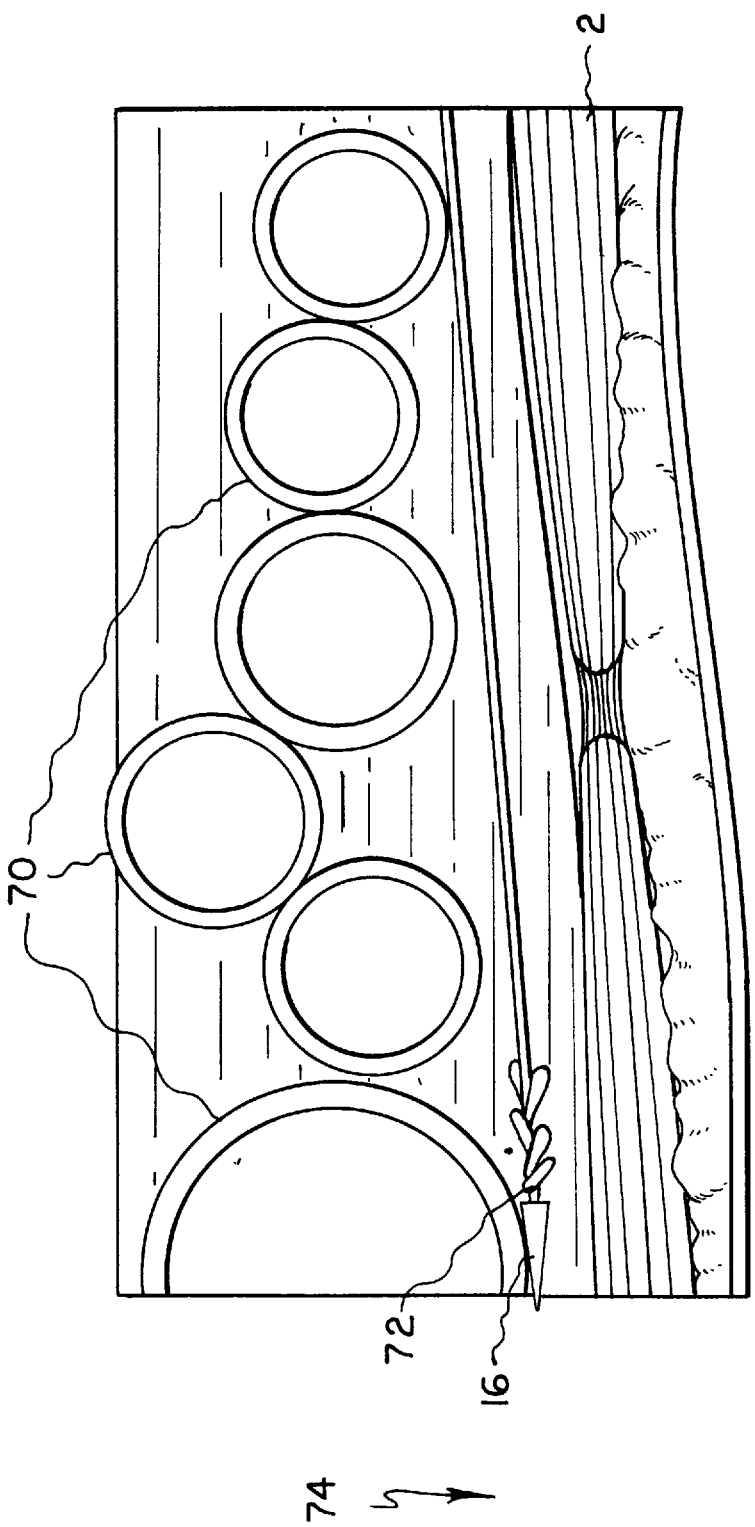
FIG. 5 is a plan view of the irrigator tube.

Cotton sheath 6 is kept damp by water 72 flowing from water source 74 through irrigator tube means 16, which is best shown in FIG. 5. FIG. 5 shows a cross-sectional view of bag 2 and intestines 70, and the placement of irrigator tube 16 therebetween. It is desirable to keep the cotton sheath 6 damp while bag 2 is in the sheath for several reasons. It is very important during surgical procedures to keep visceral organs 14 in exposed abdominal cavity 64 damp, which avoids medical complications. Also, with sheath 6 damp, sheath 6 will not adhere or stick to the visceral organs. Another advantage of keeping cotton sheath 6 damp is that it increases the thermal conductivity of the sheath, allowing heat to flow quickly from the bag 2 to the visceral organs 14.

Hand 10 applies force on sterile buffer 12, which in turn causes bag 2 to press firmly against visceral organs 14. This ensures that full contact is made between cotton sheath 6 and visceral organs 14, and proper heat transfer occurs from the bag to the visceral organs 14.

Also shown in FIG. 2 are inlet tube means 4, and outlet tube means $4^1$. The seals 76 are for attaching inlet tube 4 and outlet tube $4^1$ to bag 2. Inlet tube 4 delivers warm solution to bag 2, and outlet tube $4^1$ removes cooled solution from bag 2. Inlet and outlet tubes 4 and $4^1$, and irrigator tube 16 are made from thin walled flexible plastic tubing material, which can be polyethylene, polyurethane, or the like. The tubing 4, $4^1$ and 16 can be 2 mm to 3 mm in diameter, and 1 mm thick.

It is important to note that although bag 2 is described as being plastic, any other suitable material can be substituted therefore, such as polyethylene and polyurethane, and the bag walls $2^1$ can be about 0.5 mm thick. Further, bag 2 can be a variety of different shapes, such as rectangular, semicircular, and cylindrical; and sizes, such as large and small depending on the need, and size of the patient 68. It can also be specifically shaped to conform to a particular body organ shape, such as lung shaped, liver shaped, spleen shaped, and the like.

Figure 1:
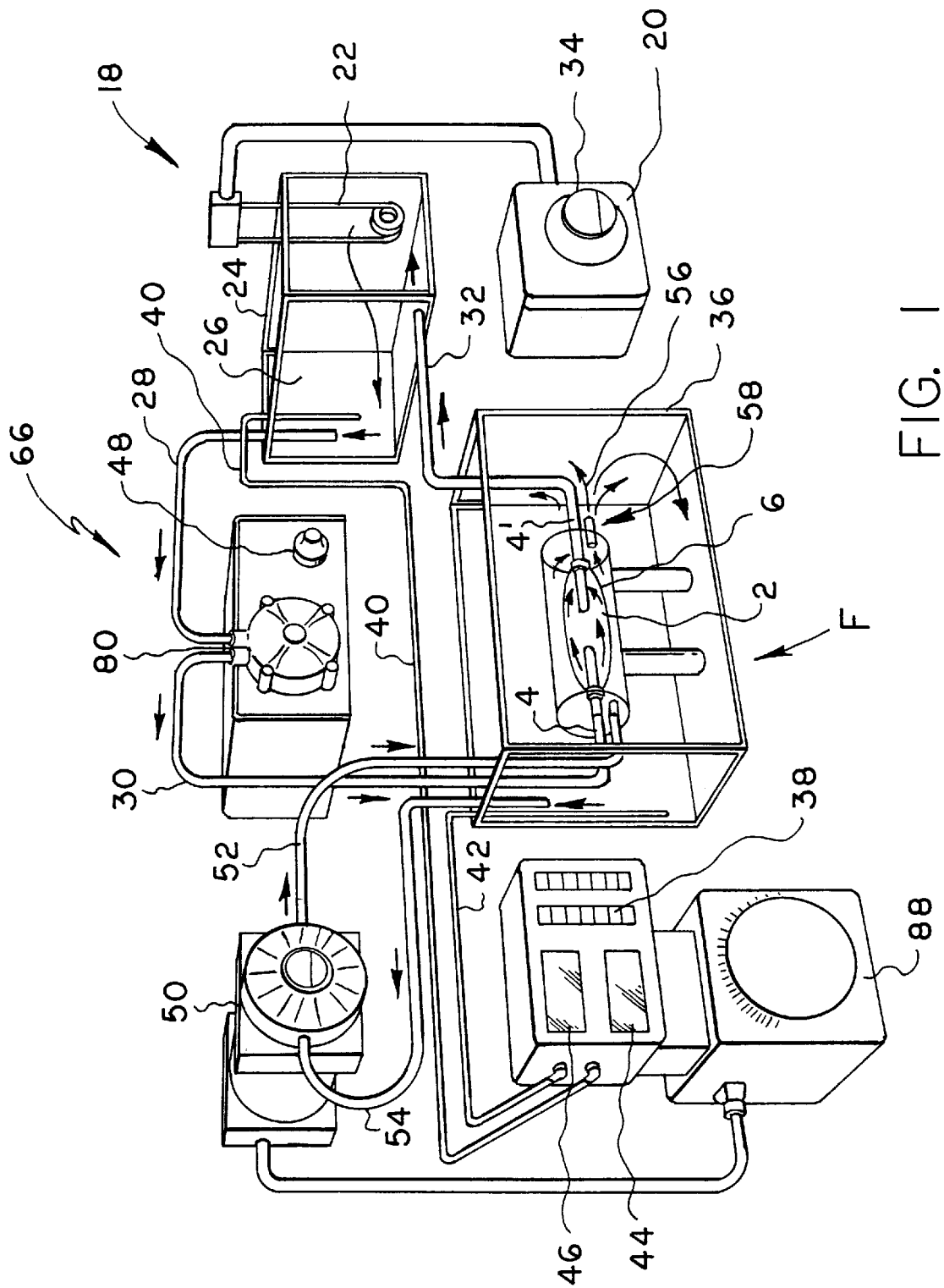
FIG. 1 is a plan view of the setup of the invention.

Shown in FIG. 1 is an illustrative diagram of the setup of the present invention. For purposes of FIG. 1, reference number 36 indicates the patient's body, which is shown schematically in FIG. 1 as a three-dimensional box. Reference number 50 indicates the patient's heart, which is shown schematically in FIG. 1 as a pump means. References numbers 52 and 54 indicate an artery and a vein respectively, which are shown schematically in FIG. 1 as tubing. Distal organs are indicated by reference number 58, which are shown schematically as being within the three-dimensional box indicating the patient's body 36. Reference number 88 indicates a heart 50 monitoring control means, which may represent the nervous system, and is shown schematically in FIG. 1 as a box having an adjusting means thereon.

Referring to FIG. 1, the entire system of the visceral body warming device is illustrated at number 18. The solution reservoir means 24 contains solution 26, and within the reservoir 24 is heating element means 22. Heat regulator means 20 controls the temperature of heating element means 22, and is adjustable by heat controller means 34, such that the temperature of heating element 22 can be adjusted. Heat moves from heating element 22 to solution 26 by conduction. Solution 26 is preferably a saline solution, but other suitable solutions such as water can be utilized in the present invention.

A solution conveying means 66 is provided which continuously circulates the solution in the following manner. Shown at 28 is the suction tube means which supplies solution 26 from the reservoir 24 to pump means 80. Pump 80 moves the solution 26 to pressurized feeder line 30, which supplies solution to inlet tube 4. Inlet tube 4 supplies the solution to the bag 2, and the solution exits bag 2 via outlet tube $4^1$. Of course, FIG. 6 shows the cotton sheath 6 surrounding bag 2. Return line 32 carries the solution exiting outlet tube $4^1$ to the reservoir 24. The solution in return line 32 is slightly cooler than the solution that entered the bag via inlet tube 4, since the solution in the bag cooled by transferring heat to the patient's body 36. The solution's temperature, upon entering reservoir 24, is increased by heating element 22. The solution, because it is once again warm, is then in a condition appropriate to enter suction tube 28 and be recirculated. The solution continues to circulate in the solution conveying means 66, for as long as necessary to prevent the onset of hypothermia in the patient 68.

FIG. 1 also shows a temperature monitor means at 38. The monitor 38 gives real time temperature measurements of body 36, as well as solution 26 in reservoir 24. There is a first temperature lead 40, which measures the temperature of solution 26 in the reservoir 24. This reading is shown on the first temperature display 44 of temperature monitor 38. There is a second temperature lead at 42, which measures the temperature of the patient's body 36. This reading is shown on the second temperature display 46. The user is then capable of seeing real time measurements of both the solution temperature at the reservoir 24, as well as the temperature of the patient's body 36. Of course, if the patient's temperature needs to be warmed more quickly, heat controller means 34 can be adjusted to raise the temperature of solution 26 in reservoir 24. The user can also regulate the speed of the pump 80, by adjusting the pump speed regulator means 48. The present invention therefore provides the user with the ability to monitor the temperatures of the solution 26 in the reservoir 24 and the patient's body 36. The user can accordingly adjust the solution temperature and rate of flow of the solution, by adjusting the heat controller 34 and pump speed regulator 48 as each case may require. For example, if the patient had an extremely low temperature, the heating element 22 temperature would be increased, and the pump 80 speed may also be increased. The result would be that the solution in bag 2 would have a constant higher temperature overall, when compared to the system operating when no such adjustments are made.

FIG. 1 also illustrates how the patient's body 2 is warmed. Heart 50 pumps blood 56 through artery 52. Heat from the bag and sheath, 2 and 6, is conducted to the blood 56, and blood 56 is warmed accordingly. The blood 56 then flows through all the distal organs 58 in the patient's body 36. The blood 56 in proximity of bag 2 is warmed, and carries the heat it absorbed from bag 2 to the entire body 36. The result is normothermic temperatures at both the visceral organs 14, as well as the distal organs 58. Blood 56 is then returned to heart 50 by vein 54, and continues to circulate in the above described manner.

There are, of course, several different ways in which the present invention can be practiced. In the event the patient's entire abdominal cavity is exposed 64, the bag 2 can be placed directly against the bowel 82, and held in place by a hand 10, as shown in FIG. 2, thus warming the splanchnic blood supply.

Figure 3:
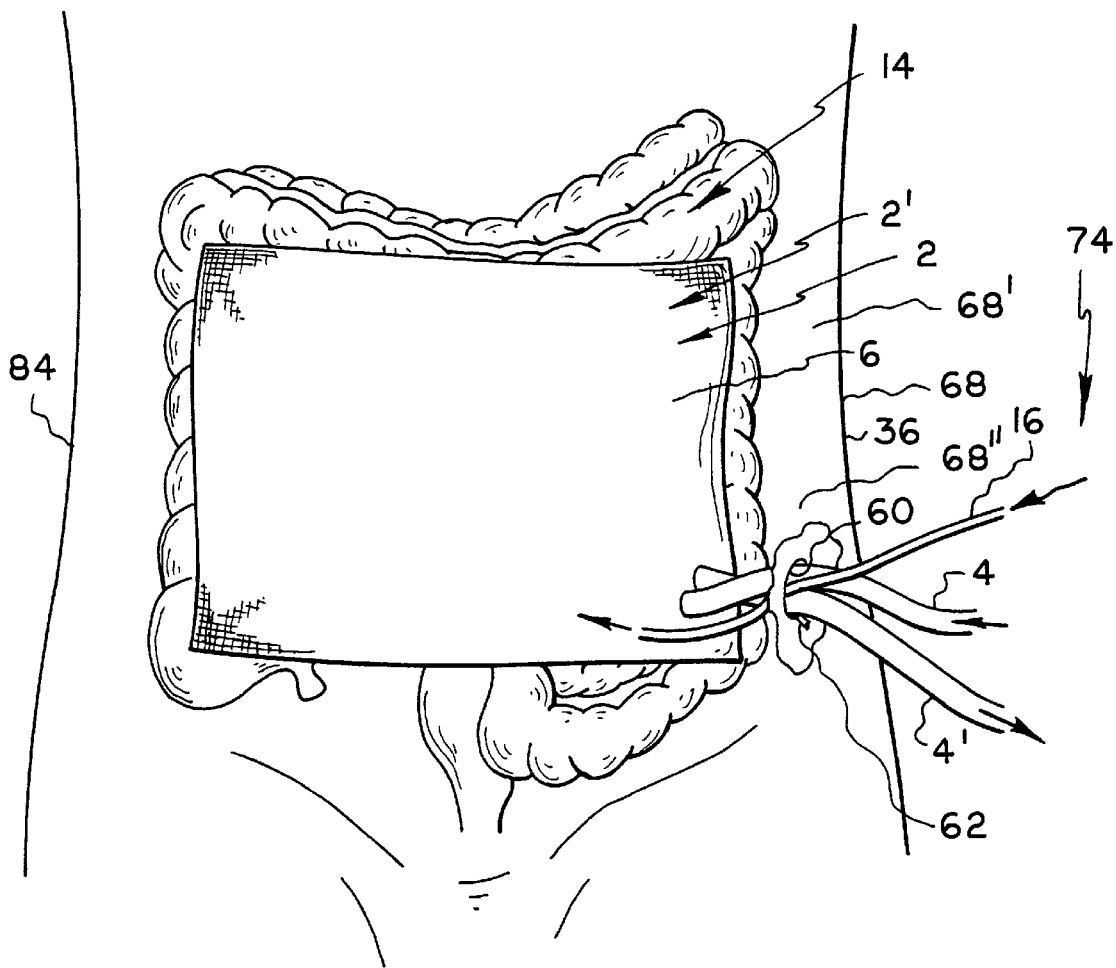
FIG. 3 is a plan view of the bag inserted into the abdominal cavity.
Figure 4:
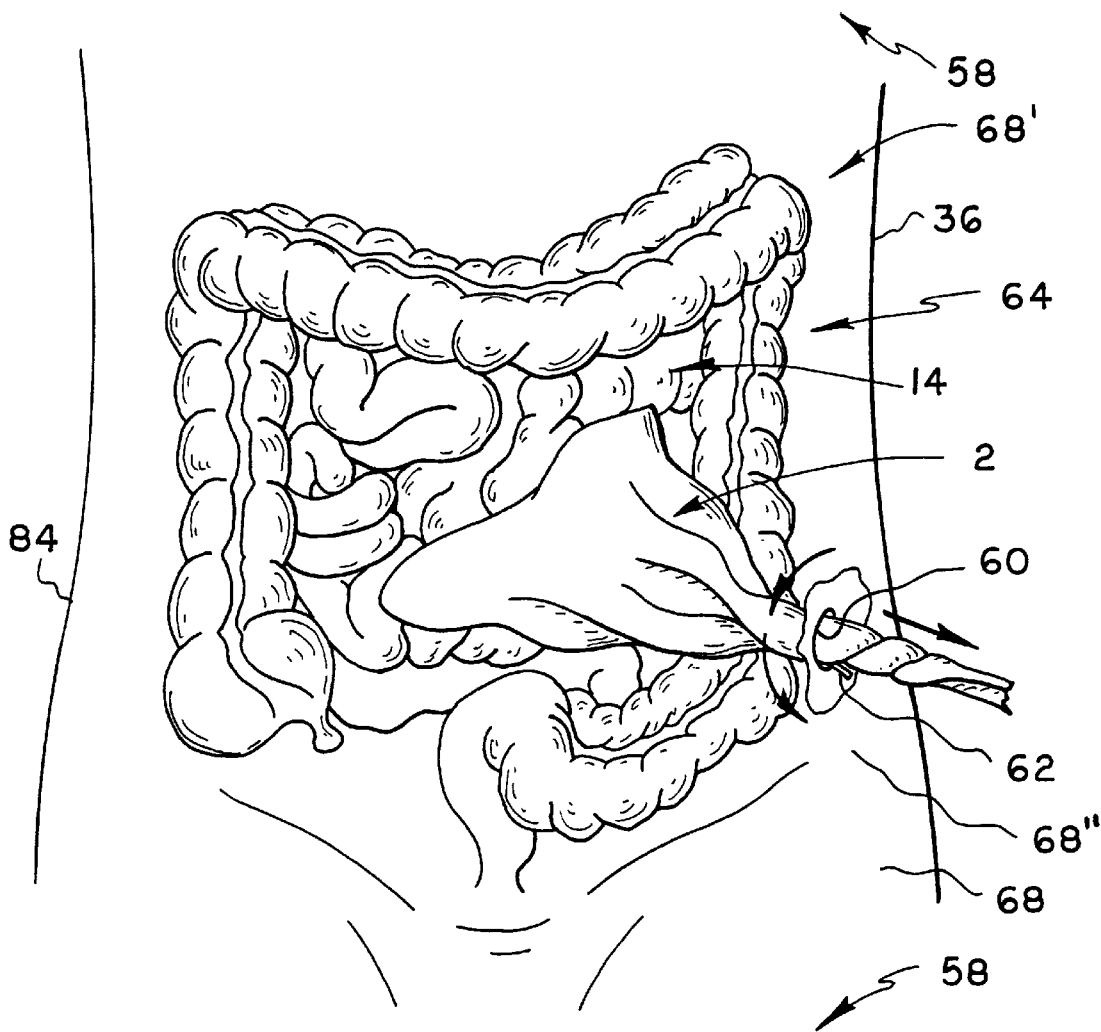
FIG. 4 is a plan view showing removal of the bag in FIG. 3.

Another embodiment of the present invention is illustrated in FIGS. 3 and 4. These figures illustrate a way to continue warming the patient 68 after the surgical procedure is completed, yet without having to reopen the patient's abdomen 68$^1$ to remove bag 2. In this application, the bag 2 will remain in the patient's abdomen 68$^1$ for an extended amount of time following surgery, and the cotton sheath 6 is not used. Rather, the bag is placed in the exposed abdominal cavity 64, and is permitted to contact directly with the visceral organs 14.

Post surgical warming is accomplished by creating bag hole 60 in the patient's side flank 68$^{11}$, before surgery is complete and before the exposed abdominal cavity 64 is sutured. Bag hole 60 can be from about 1.5 cm to about 2.0 cm in diameter. Bag tube 62 is inserted into bag hole 60. The bag 2 is placed in the patient 68, during surgery, and the inlet tube 4, outlet tube 4$^1$, and irrigator tube 16 are all positioned in and run through the bag tube 62. The exposed abdominal cavity 64 is then sutured with the bag 2 and tubes 4, 4$^1$, and 16 remaining in place. The solution 26 continues to be pumped and heat the splanchnic blood supply and visceral body organs as fully described above.

Then, after the threat of hypothermia has passed, irrigator tube 16 delivers water 72 to the bag 2 shown in FIG. 5. The water prevents bag 2 from sticking to visceral organs 14. Bag 2 is then removed by draining the solution out of it, which is accomplished by turning off pump 80. Then, the medical provider twists and feeds bag 2, inlet tube 4, outlet tube 4$^1$, and irrigator tube 16 out of bag tube 62, as shown in FIG. 4. This avoids the need of having to reopen up the patient's abdomen 68$^1$ after surgery is completed to remove bag 2. Of course, the bag hole 60 is created, tended to, and sealed after the bag 2 is removed, by medical procedures well known to those of ordinary skill in the art.

In the preferred embodiment all of the tubes 4, 4$^1$, 16, bag 2 and cotton sheath 6 are disposable, and discarded after removed from the patient 68.

In an alternative embodiment, a heating pad means 100 is used to warm and heat the splanchnic blood supply of the patient 68. The heating pad 100 may be an exothermic heating pad. Preferably heating pad 100 is thin walled plastic containing an exothermic solution. The solution can contain approximately the following amounts of the following components: activated charcoal powder 2 gr/pc; cellulose 3 gr/pc; salt 2 gr/pc; iron dust 14 gr/pc; and moisture 9 gr/pc in a mix comprising a total of 30 gr/pc. Such components are presently marketed by Scott Resources located in San Francisco, California. The heating pad 100 can be placed directly against the bowel to warm the splanchnic blood supply, and prevent hypothermia during surgery.

The heating pad 100 can also remain in the patient 68 following surgery to prevent hypothermia. A removal cord means 102 is attached to heating pad 100, and a pad hole 104 is made in the patient's flank side 68$^{11}$. A pad tube 106 is placed in the pad hole 104, and the pad is positioned on the bowel 82 or visceral organs 14, as desired. Just as with the bag above, irrigator tube 16 is placed in and runs through pad tube 106. The patient's abdomen 68$^1$ is sutured and the heating pad 100 remains in the patient 68, until the threat of hypothermia passes. The heating pad 100 is removed by first dampening heating pad 100 by supplying water to irrigator tube 16, which prevents the pad from sticking to visceral organs 14 or bowel 82. Then the medical provider pulls the removal cord 102 and irrigator tube 16, and draws heating pad 100 out pad tube 106. The pad tube 106 is removed from the patient and pad hole 104 is sutured by techniques well known to those of ordinary skill in the art. Hence, in this embodiment, the splanchnic blood supply is warmed even after surgery is complete, thus preventing post surgery hypothermia. In the preferred embodiment, the heating pad 100, pad tube 106, removal cord 102, and irrigator tube 16 are all disposable.

It is noted that although the detailed description above pertains to using this invention within a patient's body, the present invention can be used for external use on the patient's skin 84, and these uses too are intended to fall within the scope of this invention. The use of the present invention for heating the patient's skin 84 is accomplished simply by placing bag 2 or heating pad 100 against the skin 84 desired to be warmed.

It should be noted that, while the invention has been described in detail herein, the invention can be embodied otherwise without departing from the principles thereof, and such other embodiments are meant to come within the scope of the present invention as defined in following claims.

What is claimed is:

1. A body warming device comprising:

a bag containing a solution;

a reservoir for storing the solution;

a heating device in thermal communication with the reservoir and the solution; the heating device transfers heat to the solution in the reservoir to produce a warm solution;

solution conveying means in communication with the reservoir and the bag, the solution conveying means for conveying the solution from the reservoir to the bag and from the bag to the reservoir, such that the bag is warmed by the warm solution and wherein the bag is adapted to contact and transfer heat to the body;

a fluid source for supplying an irrigation fluid; and an irrigator tube in fluid communication with the fluid source and the bag for making the bag wet.

2. A body warming device according to claim 1, further comprising:

a cotton sheath for enclosing the bag; the fluid source and the irrigator tube in fluid communication with the cotton sheath and for supplying the irrigation fluid to the cotton sheath, the fluid for making the cotton sheath damp.

3. A body warming device according to claim 1, wherein the solution conveying means comprises;

a pump for pumping the solution;

an inlet for transporting the solution from the reservoir to the bag;

an outlet for transporting the solution from the bag and to the reservoir;

the pump in fluid communication with the inlet, the outlet, the bag and the reservoir, and for pumping the solution.

4. The body warming device according to claim 3, wherein the bag further comprises a thin walled plastic bag, and the solution comprises an aqueous solution.

5. The body warming device according to claim 4, wherein the bag is shaped to contour to an internal organ.

6. The body warming device of claim 5, wherein the inlet comprises a thin walled plastic tubing, and the outlet comprises a thin walled plastic tubing, and wherein the irrigator tube is made of thin walled plastic tubing.

7. The body warming device of claim 6, further comprising:

mechanism adapted to be interdisposed in a hole in a body of a patient; the inlet, the outlet, and the irrigator tube positioned inside the mechanism, and the bag adapted to be positioned in the body of a patient.

8. A method for warming a body comprising the steps of:

providing a bag for containing a solution;

storing the solution in a reservoir;

heating the solution in the reservoir and producing a warm solution;

conveying the solution from the reservoir to the bag and from the bag to the reservoir, such that the bag is warmed by the warm solution;

contacting the bag with the body and warming the body by transferring heat from the warm solution to the body;

supplying an irrigation fluid from an irrigator tube; and irrigating the bag with the fluid from the irrigator tube, to make the bag wet.

9. A method for warming a body according to claim 8, further comprises the step of:

enclosing the bag in a cotton sheath.

10. A method for warming a body according to claim 8, where the step of conveying the solution comprises pumping the solution from the reservoir to an inlet fluidly connected to the bag, through the bag to an outlet fluidly connected to the bag, and back to the reservoir.

11. A method for warming a body according to claim 10, comprising the step of constructing the bag of a thin walled plastic bag, and making the solution an aqueous solution.

12. A method for warming a body according to claim 11, further comprising the step of constructing the bag in a shape which contours to an internal organ of the body.

13. A method for warming a body according to claim 12, comprising the further steps of:

constructing the inlet and the outlet of a thin walled plastic tubing; and supplying the irrigation fluid to the cotton sheath through the irrigator tube, the irrigator tube being made of thin walled plastic tubing.

14. A method for warming a body according to claim 13, comprising the following steps:

making a tube hole in side flank of the body;

placing a tube hole mechanism in the tube hole;

positioning the inlet and the outlet in the tube hole mechanism, and positioning the bag in the body, the tube hole mechanism for permitting the inlet, the outlet, and the bag to be removed from the body.

15. The method according to claim 14, further comprising the step of positioning the irrigator tube in the tube hole mechanism.

16. A body warming device comprising:

a heating pad;

an aqueous fluid;

an irrigator tube in fluid communication with the heating pad, for supplying the aqueous fluid to the heating pad;

a removable cord attached to the heating pad;

a pad tube adapted to be interdisposed in a hole in a body of a patient; the removable cord and the irrigator tube positioned inside the pad tube, and the heating pad adapted to be positioned inside the body, the pad hole for permitting the heating pad, the removable cord, and the irrigator tube to be removed from the body.

17. A body warming device according to claim 16, wherein the heating pad comprises an exothermic heating pad.

* * * * *